(12) United States Patent
West (10) Patent No.: US 11,877,719 B2
(45) Date of Patent: Jan. 23, 2024

(54) BONE PLATE WITH ORIENTATION INDICATOR AND POSITIONAL ADJUSTMENT MECHANISM

(71) Applicant: OrthoNovis, Inc., Palm Coast, FL (US)

(72) Inventor: Kenneth West, Flagler Beach, FL (US)

(73) Assignee: ORTHONOVIS, INC., Palm Coast, FL (US)

(*) Notice: Subject to any disclaimer, the term of this patent is extended or adjusted under 35 U.S.C. 154(b) by 189 days.

(21) Appl. No.: 16/912,186

(22) Filed: Jun. 25, 2020

(65) Prior Publication Data

US 2020/0405435 A1 Dec. 31, 2020

Related U.S. Application Data

(60) Provisional application No. 62/866,193, filed on Jun. 25, 2019.

(51) Int. Cl.
| | | |
|---|---|---|
| *A61B 17/80* | (2006.01) |
| *A61B 90/94* | (2016.01) |
| *A61B 17/86* | (2006.01) |
| *A61B 90/00* | (2016.01) |
| *A61B 17/68* | (2006.01) |

(52) U.S. Cl.
CPC .......... *A61B 90/94* (2016.02); *A61B 17/8004* (2013.01); *A61B 17/8057* (2013.01); *A61B 17/8061* (2013.01); *A61B 17/8615* (2013.01); *A61B 2017/681* (2013.01); *A61B 2090/3966* (2016.02)

(58) Field of Classification Search
CPC .......... A61B 17/8004; A61B 17/8057; A61B 17/8061; A61B 17/8615; A61B 17/8605
See application file for complete search history.

(56) References Cited

U.S. PATENT DOCUMENTS

| | | | |
|---|---|---|---|
| 6,322,562 B1 | 11/2001 | Wolter | |
| 6,623,486 B1* | 9/2003 | Weaver | A61B 17/8625 606/291 |
| 8,398,687 B2* | 3/2013 | Vasta | A61B 17/8061 606/291 |
| 8,852,249 B2* | 10/2014 | Ahrens | A61B 17/8014 606/291 |
| 8,992,582 B1 | 3/2015 | Knoepfle et al. | |
| 9,486,262 B2* | 11/2016 | Andermahr | A61B 17/809 |
| 10,251,687 B2* | 4/2019 | Guo | A61B 17/848 |
| 10,383,668 B2* | 8/2019 | Rutledge | A61B 17/8085 |

(Continued)

*Primary Examiner* — Anu Ramana
(74) *Attorney, Agent, or Firm* — Farber LLC (57) ABSTRACT

A bone plate for the compression of a fracture site or osteotomy of a bone includes a bone plate assembly having a plate body shaped and configured for an anatomical location on a patient. The plate body has an upper surface, a lower, bone contacting surface, medial and lateral side surfaces connecting the upper and lower surfaces and at least one screw hole extending through the plate body. The bone plate further includes an access hole extending between the upper and lower surfaces and defining an inner surface shaped to indicate the anatomical location on the patient. This configuration allows the surgeon to easily determine which bone plate should be used for the operation, thereby avoiding costly mistakes during surgery. The bone plate may further include an adjustable screw hole for repositioning the bone plate relative to the fracture site.

9 Claims, 10 Drawing Sheets

(56) References Cited

U.S. PATENT DOCUMENTS

| | | | |
|---|---|---|---|
| 2004/0116930 A1* | 6/2004 | O'Driscoll | A61B 17/8061 606/907 |
| 2006/0085000 A1* | 4/2006 | Mohr | A61B 17/8085 606/280 |
| 2008/0161860 A1* | 7/2008 | Ahrens | A61B 17/8014 606/280 |
| 2015/0039033 A1* | 2/2015 | Biedermann | B22F 3/24 264/154 |
| 2016/0324552 A1* | 11/2016 | Baker | A61B 17/80 |
| 2017/0319249 A1* | 11/2017 | Guo | A61B 17/80 |
| 2018/0049788 A1* | 2/2018 | Rutledge | A61B 17/8061 |
| 2019/0053864 A1* | 2/2019 | Cook | A61B 17/7059 |

* cited by examiner

BONE PLATE WITH ORIENTATION INDICATOR AND POSITIONAL ADJUSTMENT MECHANISM

CROSS-REFERENCE TO RELATED APPLICATIONS

This application claims the benefit of U.S. Provisional Application Ser. No. 62/866,193, filed Jun. 25, 2019, the entire disclosure of which is incorporated by reference for all purposes as if copied and pasted herein.

FIELD OF THE INVENTION

The present invention relates to orthopedic internal fixation devices, and more particularly to a bone plate for the fixation and compression of fractures incorporating an orientation indicator and a positional adjustment screw assembly.

BACKGROUND OF THE INVENTION

Bone fractures can occur due to a number of reasons: disease, such as osteoporosis; overuse by repetitive motion, which can, for example, cause stress fractures in athletes; trauma, such as by a fall or car accident; and the physiological changes that come with the aging process. An osteotomy is a surgical operation in which a bone is excised to shorten, lengthen or change the alignment of the bone. Osteotomies are often performed to correct bone deformities. Proper healing of both bone fractures and osteotomies can involve open reduction and internal fixation, where the bone fragments are repositioned in their normal alignment and then held together to facilitate healing.

A bone plate is a type of internal fixator that is surgically implanted and may generally be used to stabilize bone fragments and carry out osteosynthesis. For non-unions, such as joint fractures, simple shaft fractures and osteotomies, it is desirable that the bone itself supports and stabilizes rigid osteosynthesis. In cases of comminuted fractures, it is desirable that the bone ends be aligned and stabilized, while the proper length of the bone is maintained in flexible osteosynthesis.

Bone plates are often used to aid in the treatment of different bone fractures and osteotomies. Typically, the bone plate will be specifically designed for a particular anatomical location on the patient. In addition, since the medial and lateral sides of the left and right body parts are usually reversed relative to each other, bone plates are typically sized and shaped specifically for the left or right side of the patient. For example, a wrist plate is shaped and dimensioned for reduction and compression of fracture(s) in and around the arm and wrist, such as a distal radius or ulna fracture. Wrist plates typically come in two versions that may have different shapes and sizes, or they may be designed with screw holes having different angles relative to the plate (i.e., a right wrist plate designed for the right wrist and a left wrist plate for the left wrist).

Although left and right bone plates often have a different configuration to accommodate the appropriate side of the patient, the overall form of these two bone plates may appear similar to a health care provider in a busy operating room. In some cases, for example, the actual shape of the left and right bone plates may appear identical, with the main difference being the angle of the screw holes formed within the plates. Therefore, there are times when the surgeon unfortunately attempts to implant the wrong plate on a patient (e.g., left wrist plate on the right wrist, or vice versa). If the mistake is realized prior to implantation, the surgeon must interrupt the procedure to obtain the correct anatomical plate. In some instances, however, the mistake may not be realized until the bone plate is partially or completely fixed to the bone(s) at or around the fracture site, which may require the surgeon to remove the bone plate and repeat the entire procedure with the anatomically correct plate.

Even when the correct anatomical bone plate has been selected, bone fracture procedures can be complicated. The bone plate is designed to hold the bone fragments together in their normal alignment to facilitate healing, while minimizing interference with the patient's mobility after the fracture has completely healed. After the surgical site has been accessed and the fracture reduced, the surgeon must place the bone plate in a precise location relative to the fractured bones to optimize stability and healing of the fracture, and to ensure that the patient has sufficient mobility and function after the fracture has healed. Typically, this is accomplished by positioning the bone plate at an approximate location at or around the fracture site (to the best of the surgeon's ability), and then driving one or more bone screws through the bone plate and into the bone fragments to fix the bone plate to the fragments.

Unfortunately, it is often difficult for the surgeon to determine the desired position of the bone plate before one or more of the bone screws have been driven into the bone. Once this occurs, however, repositioning the bone plate typically requires the surgeon to retract the bone screw from the bone fragment and the plate. Not only does this cause additional trauma to the patient, but it also creates additional and unnecessary screw holes in the bone fragments. These bone fragments may already be broken into relatively small pieces. Thus, the creation of additional unnecessary holes makes it significantly more difficult for the surgeon to find another suitable location in the bone fragment(s) in which to drive the bone screws and thereby reposition the bone plate.

Accordingly, it is desirable to provide improved bone plates that make osteotomies and fracture procedures quicker, easier and more efficient for the surgeon and the hospital staff. More importantly, what is needed is a bone plate that reduces mistakes during surgery and also allows for easier and more effective repositioning of the bone plate prior to final implantation at or around the fracture site.

BRIEF SUMMARY OF THE INVENTION

The present disclosure provides a bone plate for the compression of a fracture site or osteotomy of a bone. The bone plate includes a plate body with an upper surface, a lower, bone contacting surface, medial and lateral side surfaces connecting the upper and lower surfaces and at least one screw hole extending through the plate body. The bone plate further includes an access hole extending between the upper and lower surfaces. The access hole defines an inner surface shaped to indicate an anatomical location on the patient. This configuration allows the surgeon and/or hospital staff to easily determine whether the bone plate is the correct plate for that procedure, thereby avoiding costly mistakes during surgery. The access hole can also serve to confirm the correct orientation or placement of the plate.

In one embodiment, the bone plate assembly includes either a left side bone plate or a right side bone plate. The access hole serves as an orientation indicator, with the inner surface of the access hole having a shape or configuration that indicates the proper anatomical target and/or orientation of the plate, such as the shape of a different alphabet letter to distinguish a right bone plate from a left bone plate. In the exemplary embodiment, the right plate access hole is in the shape of an R and the left plate access hole in the shape of an L. The access holes are large enough to allow the surgeon or hospital staff to easily recognize the correct bone plate for the left or right side in the chaos of a busy operating room. In certain embodiments, the access holes are large enough to be imaged under fluoroscopy so that the hospital staff can confirm after the operation that the correct plate has been implanted.

Of course, other shapes may be used to designate "left" and "right" or other target anatomical site (e.g., anterior or posterior, lateral or medial, etc.). For example, the access holes may have inner surfaces shaped as numbers (e.g., "1" for right and "2" for left), arrows (e.g., an arrow having an arrowhead pointing towards the left side for the left plate and vice versa), pictures (e.g., pictures of right or left wrists or pictures of other anatomical locations on the patient's body), letters other than R and L, such as A and P for anterior/posterior or M and L for medial/lateral, or other distinguishing markings, such as symbols, texts, characters, emojis and the like. As such, the access holes may serve as directional markers or navigation tools that may assist with the proper location and/or proper placement of the plate during or after implantation.

In certain embodiments, the access hole is disposed on the bone plate in a location suitable for accessing the underlying bone fragments after the bone plate has been positioned at the fracture site and fixed to one or more of those bone fragments. In these embodiments, the surgeon may use the access hole to, for example, deliver a bone graft or synthetic graft material through the bone plate and onto the underlying bone to enhance healing at the fracture site.

In one embodiment, the right and left plate bodies are configured for compression of a distal radius fracture around the patient's wrist. Thus, each of the plate bodies comprises an elongate proximal portion connected to a distal portion that is inclined relative to the proximal portion. The proximal portion generally overlies the bones of the arm (i.e., the radius) while the distal portion overlies the wrist. The distal portion is preferably wider than the proximal portion relative to the longitudinal axis of the bone plate. In these embodiments, the access hole preferably resides in the distal portion of the plate body.

In another aspect of the invention, a bone plate assembly for compression of a fracture site or osteotomy of a bone comprises a bone plate and at least one bone screw. The bone plate includes an upper surface, a lower, bone contacting surface and at least one screw hole extending through the plate body. The screw hole includes an opening for receiving a bone screw and the upper surface of the plate body includes a recessed portion surrounding the screw hole. The bone screw comprises a head extending into an elongated shank. The opening of the screw hole is smaller than the outer surface of the head and larger than the radius of the elongated shank and the recessed portion of the upper surface has an inner surface defining an opening in the upper surface of the bone plate that is larger than the outer surface of the head of the bone screw.

The recessed surface of the screw hole creates a gap substantially around the entire surface of the bone screw head, allowing for movement of the head relative to the plate when the shank extends through the screw hole opening and the screw head resides within the recessed portion. This configuration allows the plate to be repositioned relative to the bone screw after the bone screw has been at least partially driven into the patient's tissue or bone at or around the fracture site. In a preferred embodiment, the bone plate can be adjusted in the longitudinal direction and in any direction transverse to the longitudinal axis (i.e., 360 degrees) relative to the bone screw. The ability to make small or "micro" adjustments to the position of the bone plate after it has been at least partially secured to a bone fragment minimizes trauma to the patient during the procedure. In addition, it avoids the creation of additional and unnecessary screw holes in the bone fragments, thereby making the overall operation faster and easier for the surgeon.

The present invention is also directed to a method of affecting compression of a fracture site or osteotomy of a bone. The above-described bone plating system is used, wherein the fracture is reduced and the appropriate bone plate (e.g., left or right) is selected with the orientation indicators or access holes. The bone plate is then positioned in an approximate location over the fractured bone. The bone screw is placed through the screw hole opening and partially driven into the tissue or bone until the screw head is positioned within the recessed surface of the screw hole (but not completely tightened). The surgeon may then reposition the bone plate relative to the screw and the fracture site. Once the final position has been selected, the bone screw is driven further into the tissue until the lower surface of the screw head is secured firmly to the recessed surface of the screw hole. In certain embodiments, additional bone screws will then be driven through additional screw holes in the bone plate to secure the bone plate to other portions of the fracture site.

In another aspect of the invention, the bone plate further includes a second bone screw hole that allows either a locking screw or a non-locking screw to be selected for use within the same screw hole to affect axial compression. This allows the surgeon to take into account the location, health and quality of the bone at the site when selecting the bone screw. If a locking screw is used, the fixation function and the compression function within the second screw hole are performed simultaneously. For the patient, these structural and functional elements provide a number of advantages. The number of bone screws used to treat the fracture can be greatly reduced, which means the bone is perforated less and the surgery can be simplified. Also, fewer holes in the plate mean that the dimensions of the bone plate can be reduced while maintaining strength. In addition, as the holes take up less space in the plate, they and their respective bone screws, can be spaced closer together, which allows for increased fixation to provide a stable environment for healing to occur.

In certain embodiments, the bone plate may include a plurality of versatile screw holes that can accommodate either a locking or non-locking screw for the compression and/or fixation of a fracture site or osteotomy of a bone. Each of the versatile screw holes allows a statically placed threaded locking screw to provide both compression and fixation (i.e., locking). However, these versatile screw holes are also able to receive a non-locking screw, such as a cortex or cancellous screw, which would allow the screw to displace the plate upon insertion and achieve compression without locking. This offers the plate the advantage of providing a single screw opening that accommodates both types of screws (i.e., both locking and non-locking).

It is to be understood that both the foregoing general description and the following detailed description are exemplary and explanatory only and are not restrictive of the disclosure. Additional features of the disclosure will be set forth in part in the description which follows or may be learned by practice of the disclosure.

BRIEF DESCRIPTION OF THE DRAWINGS

The accompanying drawings, which are incorporated in and constitute a part of this specification, illustrate several embodiments of the disclosure and together with the description, serve to explain the principles of the disclosure.

The foregoing and other features of the present disclosure will become apparent to one skilled in the art to which the present disclosure relates upon consideration of the following description of exemplary embodiments with reference to the accompanying drawings.

DETAILED DESCRIPTION OF THE EMBODIMENTS

Figure 1A:
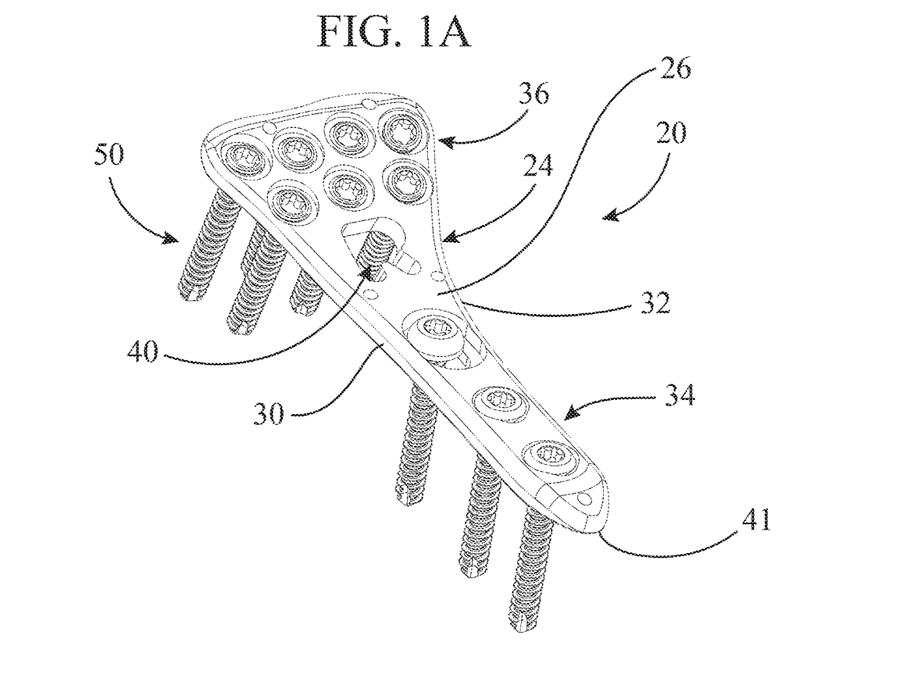
FIGS. 1A and 1B are perspective views of an exemplary embodiment of left and right configurations of a bone plate assembly having a bone plate and a plurality of bone screws according to the present invention.
Figure 1B:
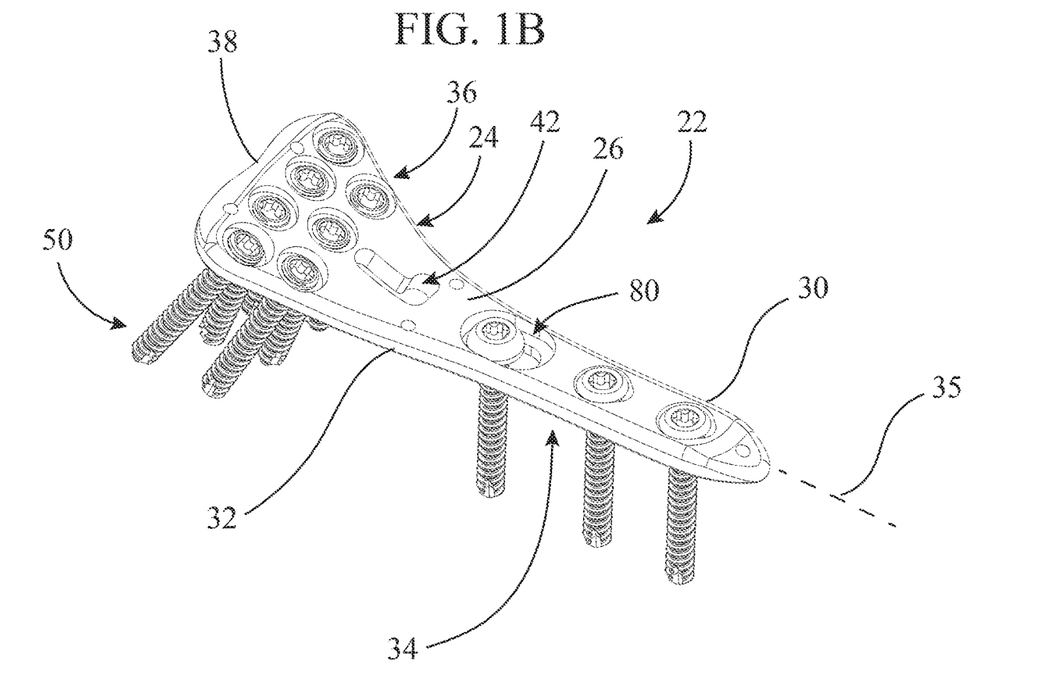

Turning now to the drawings, FIGS. 1A and 1B depict an exemplary embodiment of a bone plate assembly according to the present invention. The bone plate assembly is particularly suited for treating a fracture site on a patient's wrist, such as the dorsal surface of the distal radius bone. However, it should be understood that while the various components and the features of the present invention discussed herein are directed toward a use in connection with a fractured distal radius, such components may be modified (if necessary) to have applicability in the repair of fractures or treating osteotomies in other bones in human or animal bodies. In particular, the present invention may be used with a variety of different bone plates designed for treating fractures or osteotomies in other areas of a patient's body, such as the humerus, ulna, tibia, femur, fibula, pelvis, skull, spine, talus or other ankle bones, hand or feet bones and the like.

The bone plate assembly preferably comprises a right bone plate 20 configured for compression of a distal radius fracture on the patient's right wrist and a left bone plate 22 configured for compression of a distal radius fracture on the patient's left wrist. Each of bone plates 20, 22 have a plate body 24 with an upper surface 26, a lower, bone contacting surface 28 (see FIGS. 2A and 2B) and medial and lateral side surfaces 30, 32 connecting upper and lower surfaces 26, 28. Plate body 24 preferably further includes a substantially elongate proximal portion 34 that extends along a longitudinal axis 35 of bone plate 20, 22 and a distal portion 36 that is inclined relative to proximal portion 34. In this regard, the term "distal" refers to the direction towards the patient's hand from the patient's elbow. In particular, distal portion 36 extends upwards relative to proximal portion 34 such that upper surface 26 is slightly concave and lower surface 28 is slightly convex. In an exemplary embodiment, distal portion 36 also flares outward in the distal direction such that a distal surface 38 of distal portion 36 is the widest portion of plate body 24. Elongate proximal portion 34 comprises side surfaces that extend substantially parallel to each other from distal portion 36 to a proximal tip 41. The side surfaces of proximal portion 34 preferably taper towards tip 41 at the proximal end of plate body 26.

Of course, it will be recognized that plate body 24 may assume other shapes and configurations, depending on the specific fracture treated by the surgeon. For example, proximal portion 34 may be longer or shorter relative to distal portion (e.g., see FIG. 10) and proximal portion 34 may assume different sizes and shapes. Likewise, distal portion 36 may assume different sizes and shapes and it may substantially parallel to proximal portion 34 or extend downwardly relative to proximal portion 34 such that upper surface is convex and lower surface concave. In other embodiments, the entire plate body 24 may have substantially the same shape.

Right bone plate 20 includes a right access hole 40 and left bone plate 22 includes a left access hole 42. Access holes 40, 42 extend through plate body 24 from upper surface 26 to lower, bone contacting surface 28 and preferably serve to provide access to underlying bone or tissue. In certain embodiments, access holes 40, 42 may be used to deliver bone graft or synthetic graft therethrough during the procedure to enhance healing of the underlying bone. For example, autogenous iliac crest cancellous, corticocancellous bone graft or a synthetic graft may be used to enhance bone healing after the surgery. In other embodiments, access holes 40, 42 may be used to contain bone graft that has already been applied to the underlying bone.

Figure 2A:
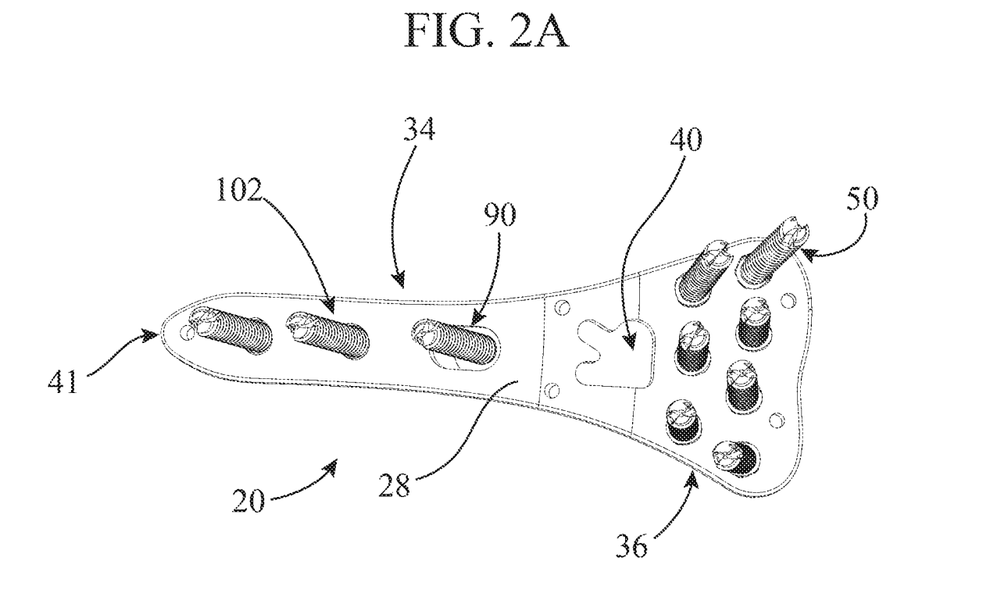
FIGS. 2A and 2B are bottom-up views of the bone plate assemblies of FIGS. 1A and 1B.
Figure 2B:
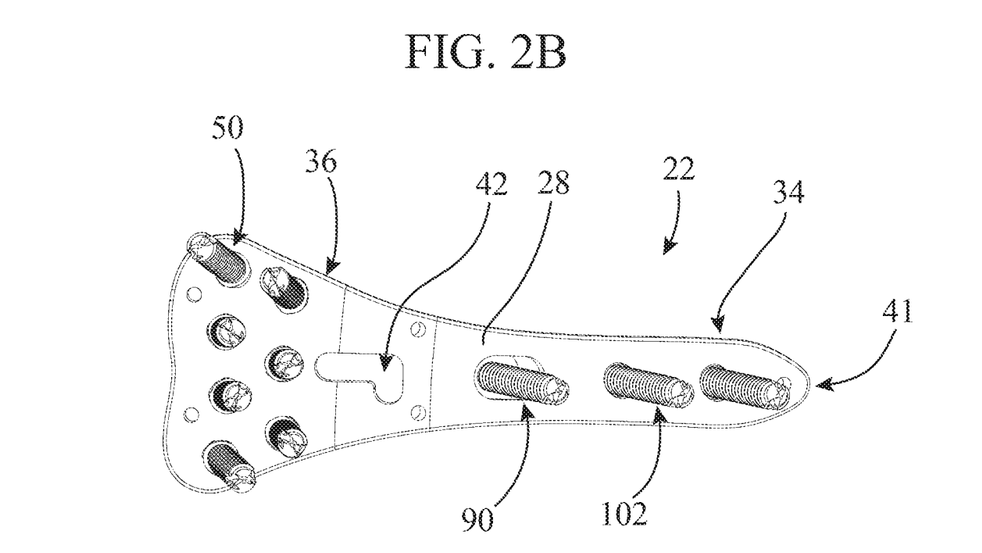

According to the present invention, right access hole 40 has an inner surface that is shaped as the letter "R" and left access hole 42 has an inner surface shaped as the letter "L". This configuration ensures that the surgeon will select the correct bone plate for the correct orientation, i.e., anatomical location, on the patient. As shown in FIGS. 1 and 2, the left and right access holes 40, 42 are clear and noticeable, and they are large enough relative to bone plate body 24 that they can easily be seen by the health care provider from either side of plate body 24. This ensures that the correct plate will be selected depending on whether the right or left wrist is being treated. In addition, holes 40, 42 are visible under fluoroscopy so that the health care provider can confirm that the correct plate has been used after the surgery has been completed and the surgical site closed up.

Of course, the invention is not limited to this configuration. For example, other shapes may be used to designate anatomical targets, such as "left" and "right", or other shapes may be used to assist with the general orientation of the plate during or after implantation (i.e., as a navigation tool to indicate proper direction or confirm proper placement through fluoroscopy, for example), such as posterior/anterior, medial/lateral, superior/inferior, proximal/distal and the like. For example, access holes 40, 42 may have inner surfaces that are shaped as numbers (e.g., "1" for right and "2" for left), arrows (e.g., an arrow having an arrowhead pointing towards the left side for the left plate and vice versa), pictures (e.g., pictures of right or left wrists or pictures of other anatomical locations on the patient's body), letters other than R and L such as P/A for posterior/anterior or M/L for medial lateral, or other distinguishing markings, such as symbols, texts, characters, emojis and the like. Alternatively, access holes 40, 42 may be shaped with various letters, names, symbols or the like to designate specific anatomical locations on the body, such as the humerus (H), distal radius (DR), tibia (T) and the like.

Bone plate assembly 10 preferably includes one or more bone screws configured to pass through screw holes in plates 22, 24 for the compression of a fracture site of a bone. In particular and as shown in FIGS. 1A and 1B, plate assembly 10 includes a plurality of screws 50 configured to extend through bone screw holes 52 (see FIG. 3) in distal portion 36 of plates 20, 22. In an exemplary embodiment, plates 22, 24 each include two rows of screw holes 52 (see FIG. 3) extending transversely to longitudinal axis 35. Due to the shape of distal portion 36, the distal row of screw holes will typically include more screw holes than the proximal row. However, it should be understood that the invention is not limited to this arrangement. For example, distal portions 36 of bone plates 20, 22 may include a single row of screw holes, a single screw hole, two screw holes, or more than the seven screw holes 52 depicted in the embodiment shown. Alternatively, a row or set of screw holes 52 may be oriented in one direction relative to longitudinal axis 35, with the other row or set of screw holes 52 facing a different direction relative to longitudinal axis 35. In addition, the sets of screw holes 52 may contain the same number of screw holes 52, or one set may have a different number of screw holes 52 than the other set.

Figure 5A:
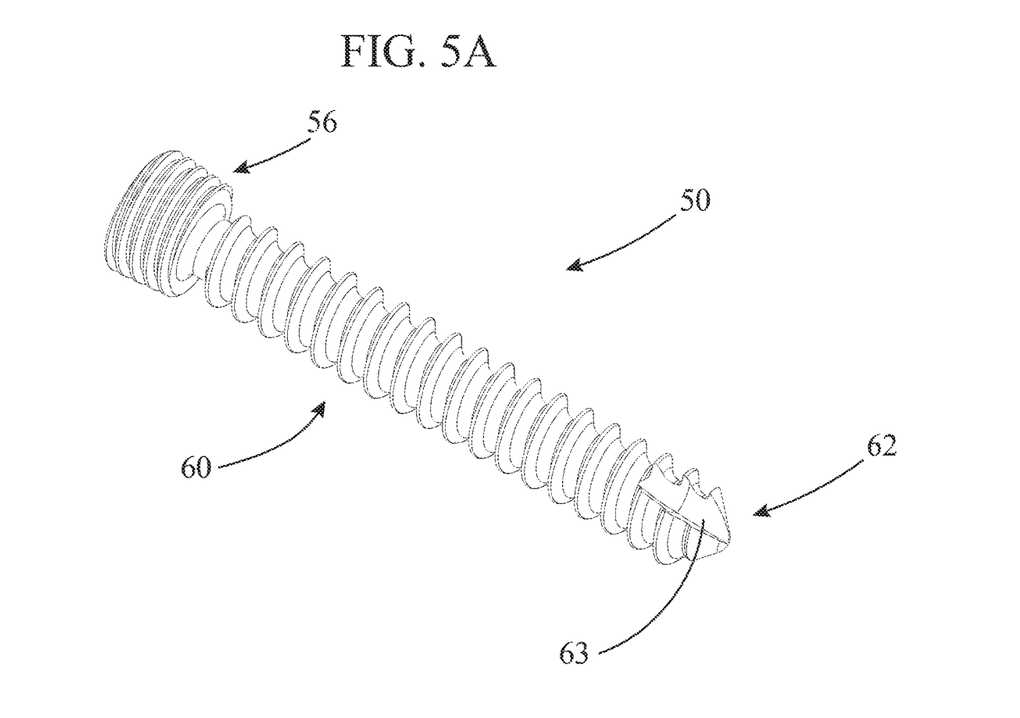
FIGS. 5A and 5B are perspective views of a tapered head screw of the bone plate assemblies of FIGS. 1A and 1B.
Figure 5B:
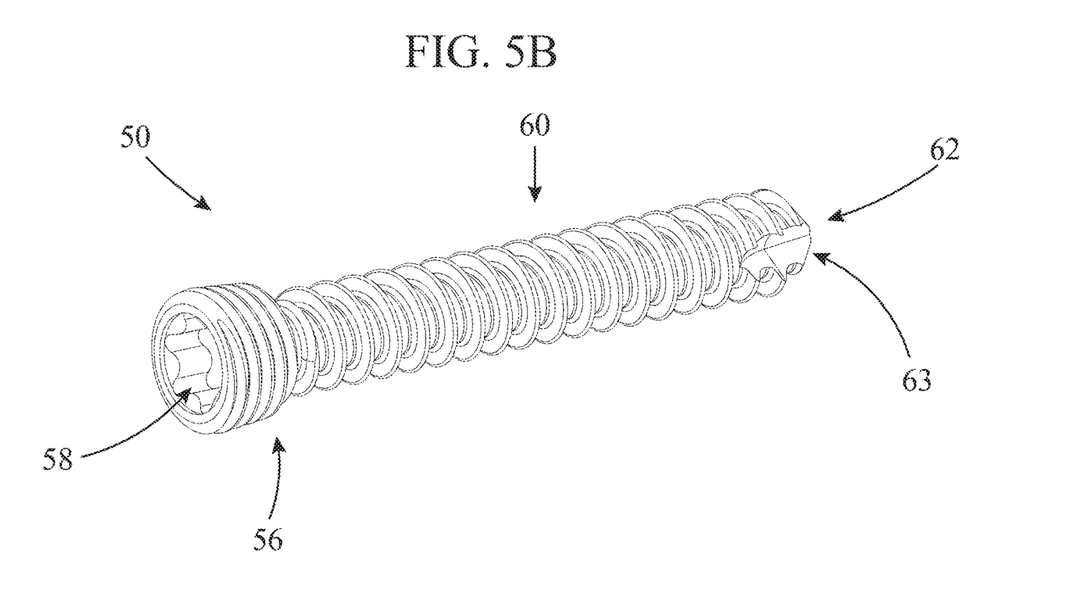

As shown in FIGS. 5A and 5B, bone screws 50 each include a head 56 with a tool-engaging opening 58, a threaded shaft 60, and a tip 62. In the exemplary embodiment, head 56 may be threaded and non-tapered, but it is understood that a variety of other configurations of bone screws 50 may be used with the present invention, such as non-threaded and/or tapered heads, rectangular, square or circular heads and the like.

Bone screws 50 may further include a notch 63 in the threaded shaft 60 extending longitudinally from tip 62 to a portion along its axis between tip 62 and head 56. In the exemplary embodiment, notch 63 extends along 1 to 20 threads, preferably about 2-4 threads of shaft 60. Notch 63 provides a cross-threaded or "stripped" distal portion of threaded shaft 60 to inhibit shaft 60 from withdrawing from tissue or bone after it has been screwed therein.

Figure 4:
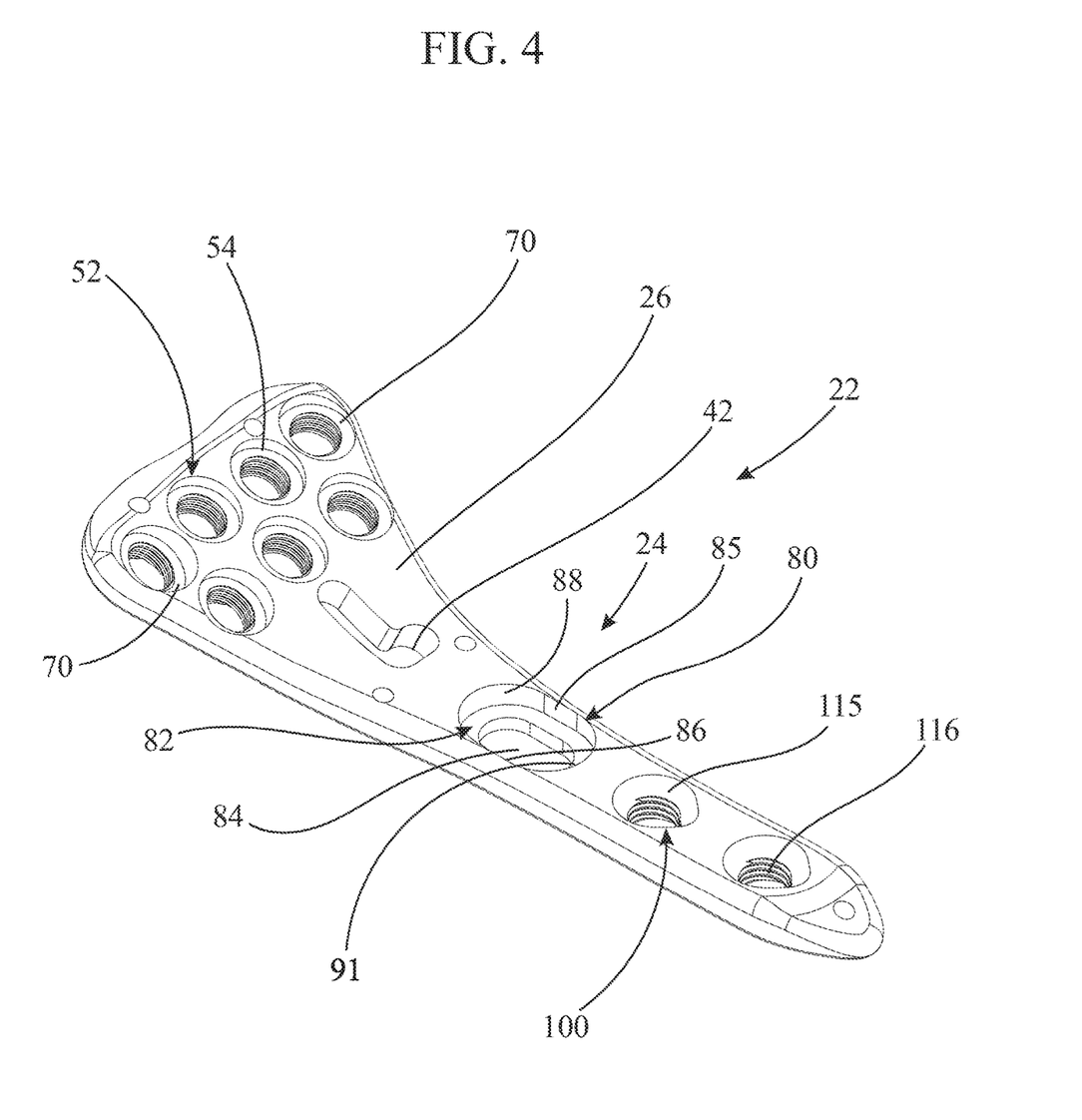
FIG. 4 is a perspective view of the bone plate of FIG. 3.
Figure 9:
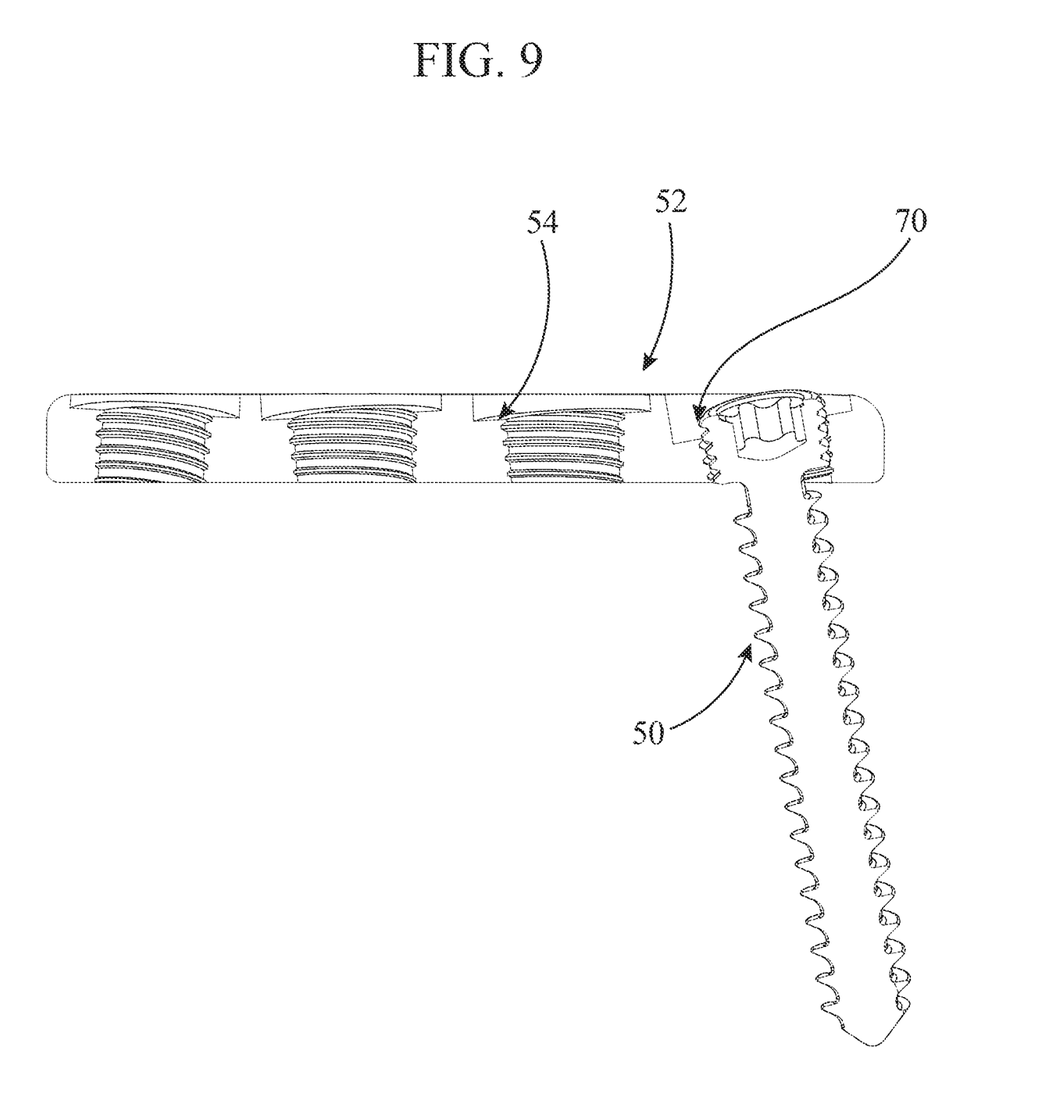
FIG. 9 is a cross-sectional view of another portion of the bone plate assembly of FIG. 1.

Referring now to FIGS. 4 and 9, screw holes 52 are recessed from upper surface 26 of each plate 20, 22, thereby defining a recessed surface 54 for receiving the head 56 of screws 50. Recessed surface 54 is preferably sized such the screw head 56 may be pressed against it without extending above upper surface 24 of plates 20, 22 to minimize contact between screw head 56 and the patient's tissue after implantation of the bone plate. Recessed surfaces 54 of screw holes 52 may be substantially parallel with upper surface 24 of distal portion 36 of plates 20, 22. In this embodiment, shafts 60 of screws 50 will extend through plates 20, 22 at an angle that is substantially perpendicular to distal portion 36. Alternatively, some or all of recessed surfaces 54 may be angled relative to upper surface 24 such that shafts 60 extend through plates 20, 22 at an angle that is not perpendicular to distal portion 36.

In an exemplary embodiment shown in FIGS. 4 and 9, the lateral and medial screw holes 52 have an inclined inner surface 70 relative to upper surface 24 of distal portion 36 of plates 20, 22 such that, when head 56 is pressed firmly against inner surface 70, the shafts 60 of screws 50 extend through plates 20, 22 at an angle relative to upper surface 24 of distal portion 36. In one embodiment, shafts 60 preferably extend distally outward from a line that runs perpendicular to distal portions 36 (see for example FIG. 1B). This angle is preferably about 5-20 degrees, more preferably about 10 degrees.

Elongate proximal portion 34 of each plate 20, 22 preferably also includes a number of screw holes for receiving bone screws. In certain embodiments according to the present invention, proximal portion 34 includes one or more adjustable screw holes 80 that allow the operator or surgeon to adjust the position of plates 20, 22 relative to the fracture site in the patient. In certain embodiments, adjustable screw holes 80 are referred to as Micro Adjustment and Translation Holes (M.A.T.H.).

Figure 8:
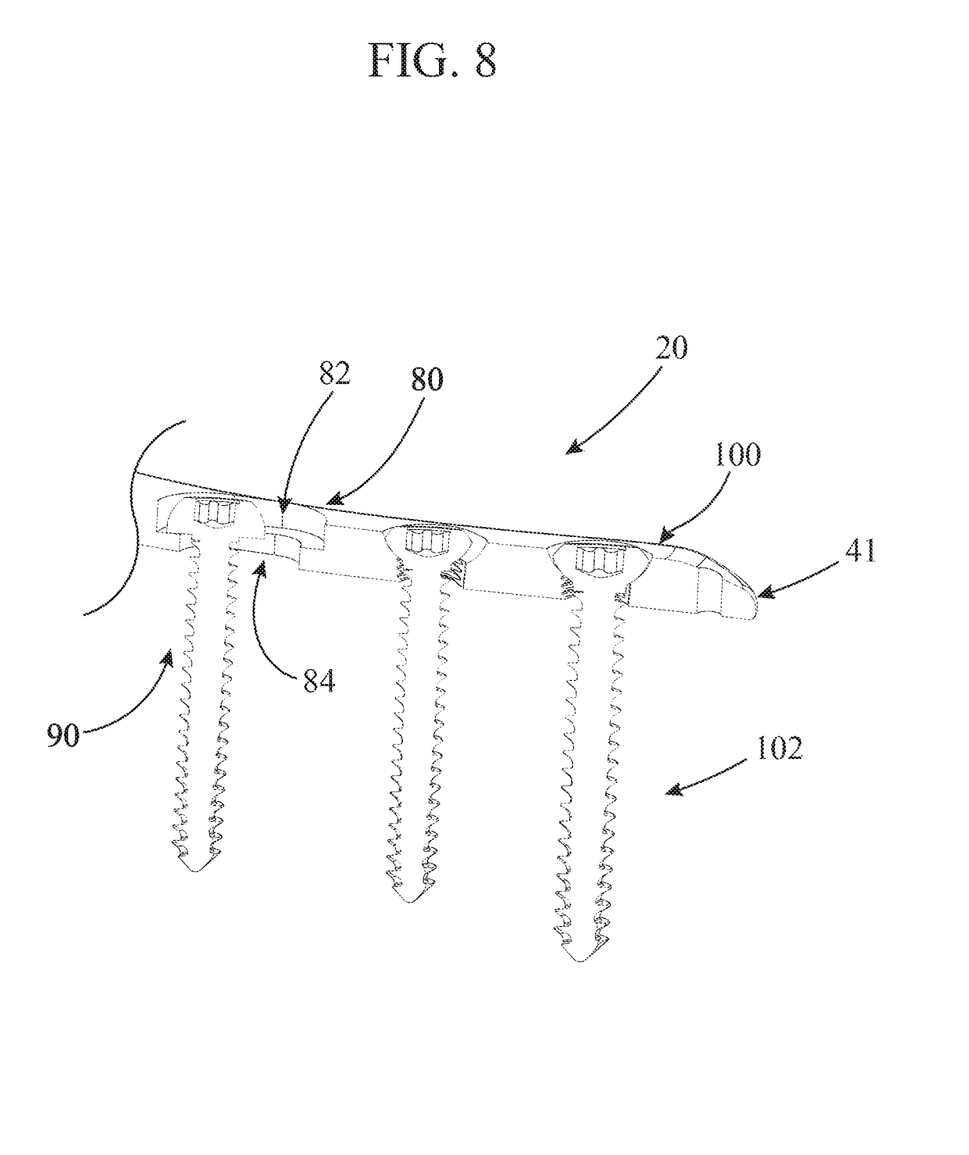
FIG. 8 is a cross-sectional view of one portion of the bone plate assembly of FIG. 1.

As shown in FIGS. 4 and 8, adjustable screw hole 80 includes a recessed portion 82 surrounding an opening 84. Recessed portion 82 is configured to receive a head of a screw while opening 84 is configured to allow passage of the shaft or elongated shank of a screw. In particular, recessed portion 82 has an outer dimension that is larger than the outer dimension of the screw head. In addition, opening 84 preferably has an outer dimension larger than an outer dimension or diameter of the screw shaft so that the screw can be adjusted relative to the bone plate 20, 22 prior to final fixation of bone plate 20, 22 to the patient's bone at or around the fracture site.

Referring again to FIG. 4, in an exemplary embodiment, recessed portion 82 has a substantially oval shape. In particular, recessed portion 82 includes elongated side surfaces 85, 86 that extend in the longitudinal direction and connect to curved proximal and distal surfaces 88, 91. Opening 84 preferably has a similar oval shape as recessed surface 82. With this configuration, a screw head may be positioned within recessed portion 82 such that the shaft of the screw extends through opening 84. The relatively larger dimensions of recessed portion 82 and opening 84 allow for adjustment of the position of bone plate 22, 24 relative to the screw and the patient's tissue or bone at or around the fracture site. In an exemplary embodiment, bone plate 22, 24 may be adjusted in a longitudinal direction (e.g., proximal or distal directions) and in at least one direction transverse to the longitudinal axis 35, preferably in any direction 360 degrees around the bone screw.

Of course, recessed portion 82 and opening 84 may have shapes other than oval, such as circular, rectangular, square and the like. In all of these embodiments, however, recessed portion 82 will have a larger outer dimension than the outer surface of the bone screw head and opening 84 will have a larger outer dimension than then radius of the bone screw shank so that bone plate can be repositioned relative to the bone screw after the bone screw has been partially driven into tissue or bone.

Figure 6A:
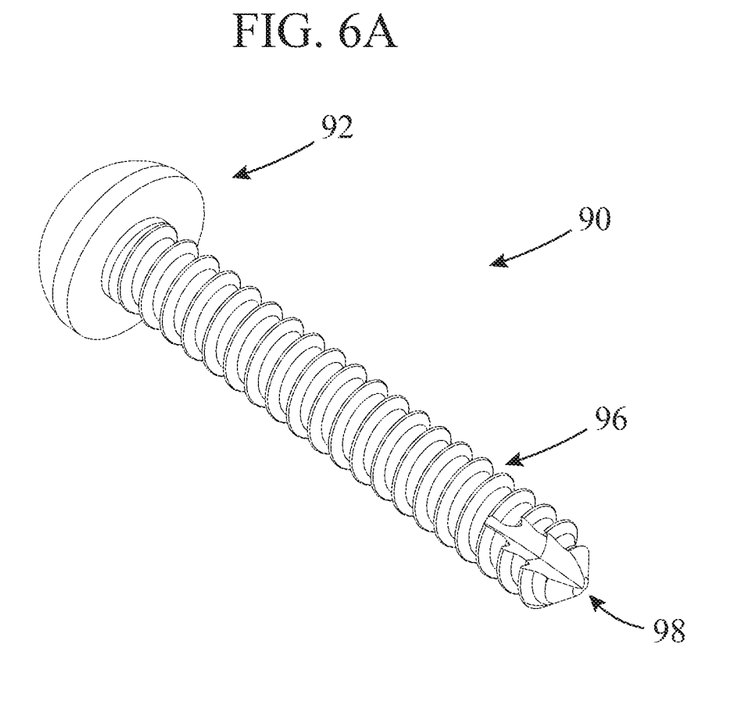
FIGS. 6A and 6B are perspective views of an adjustable bone screw according to the present invention
Figure 6B:
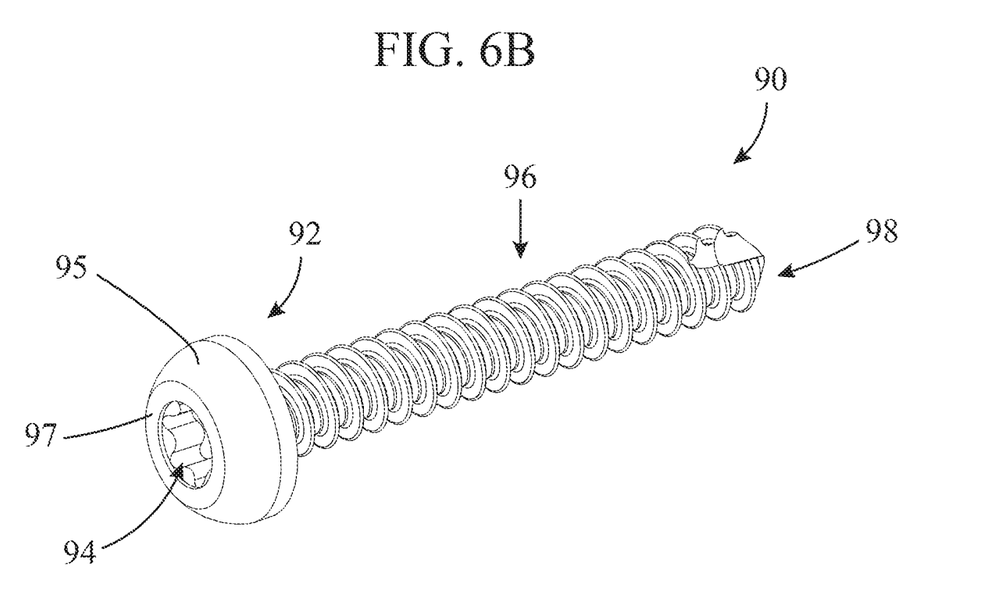

Referring now to FIGS. 6A and 6B, an exemplary adjustable bone screw 90 according to the present invention includes a tapered head 92 with a tool-engaging opening 94, a threaded shaft 96, and a tip 98. As discussed above, head 92 has a diameter less than the width and length of recessed portion 82 of plates 20, 22. In addition, shaft 96 has a diameter less than the width and length of opening 84, thereby allowing screw 90 to move relative to bone plate 20, 22 when shaft 96 extends through opening 84 and head 92 is positioned within the recess formed by surface 82 in adjustable screw hole 80.

As shown, adjustable screw 90 preferably comprises a smooth, substantially conical outer surface 95 extending from shaft 96 to a substantially flat surface 97 with tool-engaging opening 94 therein. In certain embodiments, adjustable screw 90 comprises a lag screw, such as a cancellous bone screw or a cortical screw, configured to compress fractured bone fragments together. In other embodiments, adjustable screw 90 may comprise a Fillister head screw having a flattened bearing surface. Of course, it will be recognized that other types of screws may be used in accordance with the present invention. For example, head 92 may be smooth or threaded, tapered or untapered with a round, square, hexagonal, rectangular or other suitable shape.

Bone screw assembly 10 may also include a positional adjustment mechanism in the form of an adjustable bone screw hole 80 that allows the surgeon or operator to make micro adjustments to the position of bone plate 20 relative to the surgical site prior to implantation. In use, bone plate 20 or 22 is positioned adjacent the fracture site in the patient and adjustable bone screw 90 is driven through opening 84 of adjustable bone screw hole 80 into the bone. Bone screw 90 is driven deep enough to secure screw 90 relative to the bone at or around the fracture site, but not deep enough to press the inside surface of head 92 against recessed portion 82. Preferably, bone screw 90 will be driven deep enough such that head 92 is positioned within the recess formed by recessed portion 82, but leaving a gap therebetween. Bone plate 20 may then be adjusted relative to screw 90 and the fracture site until the surgeon repositions bone plate 20 at the desired position. As the bone plate 20 is adjusted, it is moved relative to screw 90 (with screw head moving within recessed portion 82 and shaft 96 moving within opening 84). For example, bone plate 20 may be moved relative to screw 90 in the longitudinal direction or in any direction transverse to the longitudinal axis of plate body 24. Once the proper position has been determined by the surgeon, screw 90 is driven further into the tissue until screw head 92 is secured firmly against recessed surface 82, thereby locking plate 20, 22 into place relative to the tissue or bone.

Figure 7A:
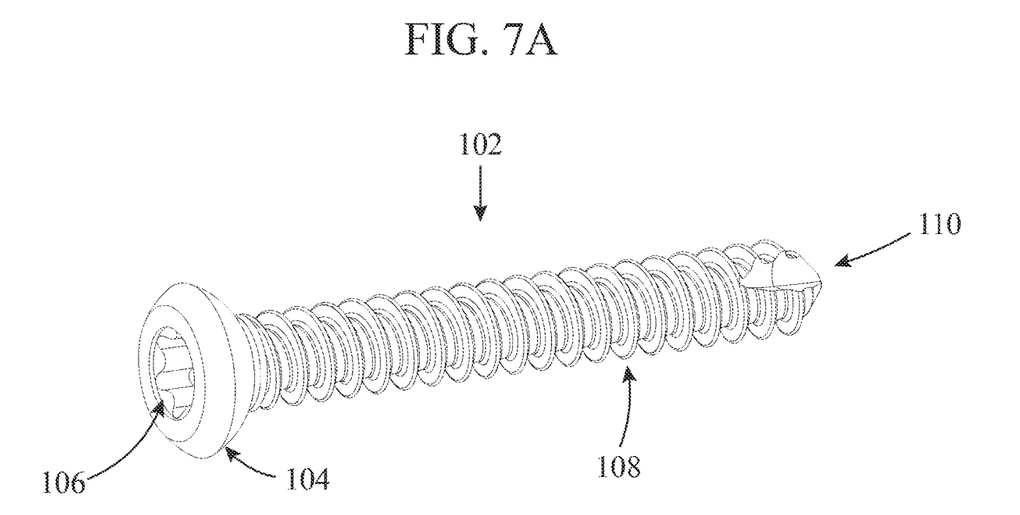
FIGS. 7A and 7B are perspective view of a non-locking cortical screw of the bone plate assemblies of FIGS. 1A and 1B.
Figure 7B:
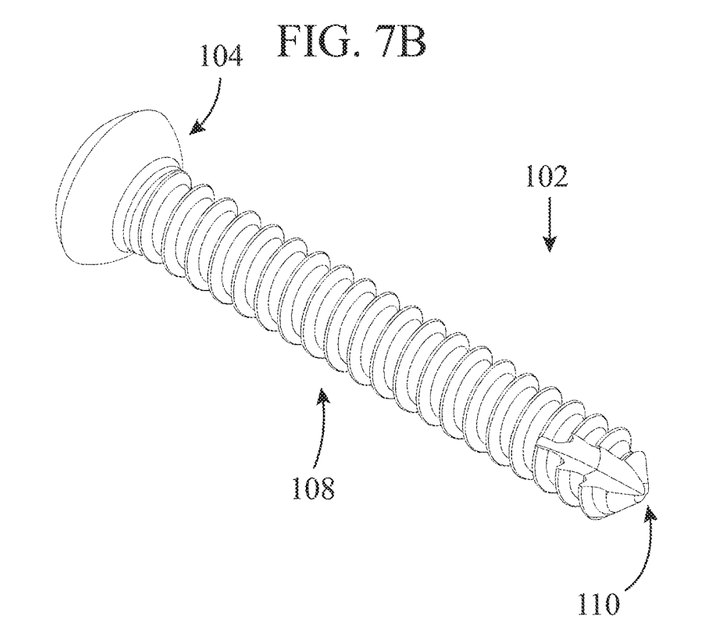

Referring again to FIG. 3, in certain embodiments, bone plates 20, 22 each preferably include one or more additional screw holes 100 positioned proximal to adjustable screw hole 90 and configured to receive bone screws 102. As shown in FIGS. 7A and 7B, the bone screw 102 may include a head 104 with a tool-engaging opening 106, a threaded shaft 108, and a tip 110. The bone screw 102 can be either locking, whereby the head 104 is threaded, or non-locking, whereby the head 104 is not threaded. Head 104 may be tapered, with a curved underside.

Screw holes 100 may comprises adjustable screw holes similar to that described above in reference to screw hole 80. In this embodiment, each of screw holes 100 will include a recessed portion (not shown) that is larger than head 104 similar to screw hole 80. The surgeon may adjust the bone plate relative to screw holes 100 to reposition plate relative to the fracture site.

Figure 3:
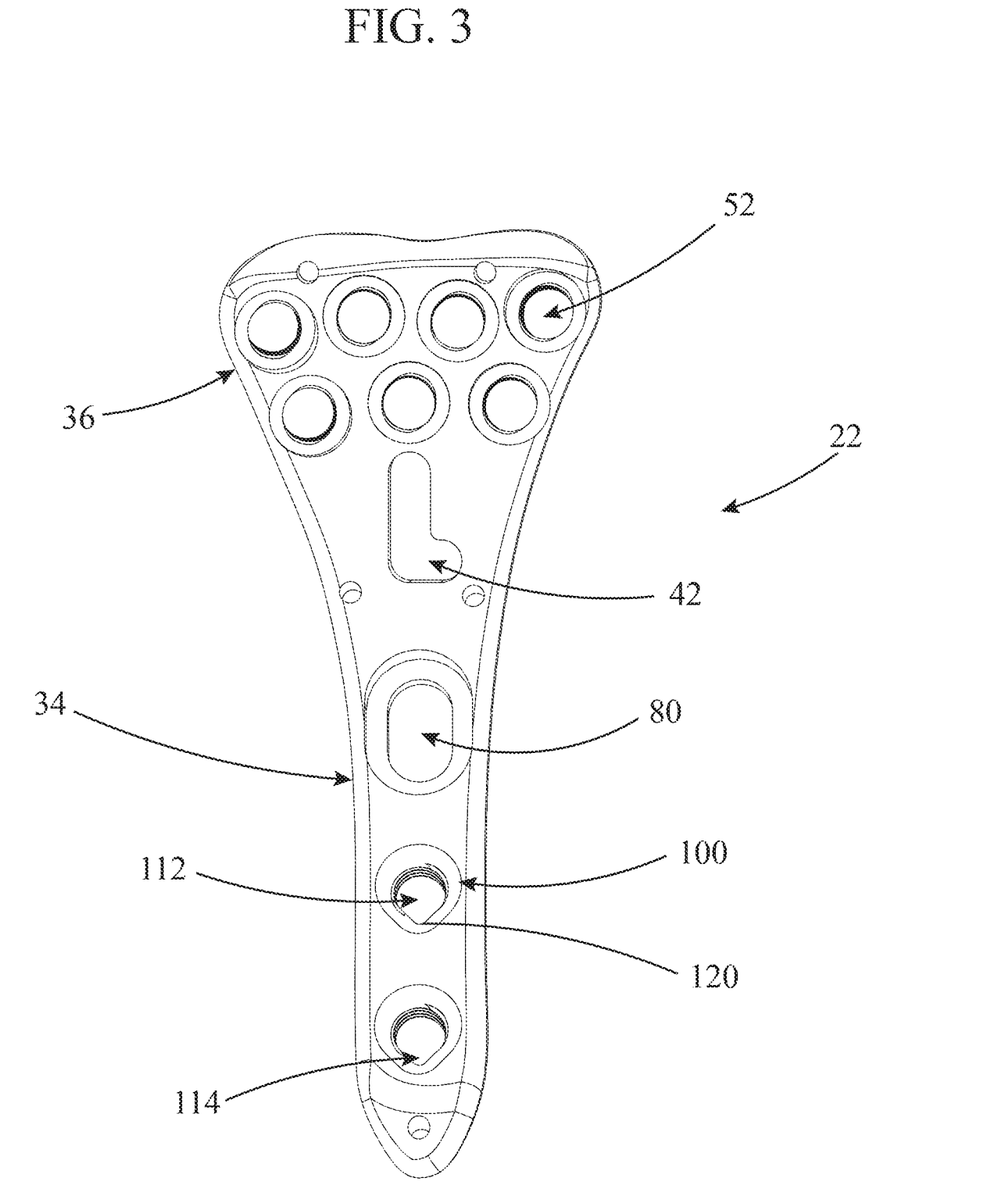
FIG. 3 is a top-down view of the left configuration of the bone plate of FIG. 1B.

In other embodiments, screw holes 100 may be versatile rather than adjustable, and can accommodate either a locking or non-locking bone screw 102. In an exemplary embodiment, the screw hole 100 may be configured with a teardrop shaped geometry, as shown in FIGS. 3 and 4. The versatile screw hole 100 may comprise a main chamber represented by a wider portion 112 of the screw hole 100, which flows into a narrower portion 114. The wider portion 112 may be a partial circular hole having a beveled edge 115 extending from the upper surface 26, and a threaded side 116 extending from the bone-contacting surface 28. This threaded side 116 is angled such that the diameter of the screw hole 100 at the upper surface 26 is larger than the diameter of the screw hole 100 at the lower, bone-contacting surface 28. In cross-section, the threaded side 116 appears conical and forms one side of a cone or V-shaped channel (not shown).

The narrower portion 114 may be non-threaded and include a compression notch 120, and extend from the wide portion 112 along the longitudinal axis 35 of the plate body 24 in a direction away from the mid-line axis ML of the plate body 24. As shown, only the curved distal end of the narrower portion 114 extends from the beveled edge 115, resulting in a groove in the upper surface 26. The groove has a radius that is smaller than the radius of the circular hole of the main chamber, or wider portion 112. As shown in FIG. 3, the combination of the wider portion or main chamber 112 and the narrower portion 114 or compression notch 120 creates a screw hole 100 that is teardrop shaped. The narrower portion 114 opens into the main chamber 112 in a smooth transition to form a continuous curved opening, as can be seen in the top-down view of FIG. 3. The main chamber 112 of the screw hole 100 accepts both locking bone screws with threaded heads and non-locking bone screws with non-threaded heads.

An advantage of this versatile hole design is that compression of the fracture or osteotomy can be obtained while using any style screw, locking or non-locking, providing the surgeon flexibility to select a screw that is most appropriate for the location, health and quality of bone. For example, the option to use a locking screw in soft or osteopenic bone to obtain compression is particularly advantageous.

An exemplary embodiment of a method of using the bone plate system 10 of the present invention to treat a bone fracture between two bone segments will now be described. Once the fracture is reduced, the health care provider selects the appropriate bone plate for compression of the fracture. Access holes 40, 42 conveniently indicate whether a particular bone plate is configured for the left or right side of the patient's body. The bone plate 20, 22 is positioned to span the fracture and adjustable screw 90 is driven through opening 84 of adjustable screw hole 80 and into the tissue or bone at or around the fracture site so that it is partially tight, but leaves enough room for movement of bone plate 20, 22 relative to screw 90.

The system 10 may further include a number of suitable drill guide instruments (not shown) designed to cooperate with the tool-engaging openings in the various screw heads described herein, such as the one described in commonly assigned, co-owned U.S. Pat. No. 10,226,287, filed Dec. 23, 2014 and entitled "BONE PLATE WITH VERSATILE SCREW HOLES", the complete disclosure of which is hereby incorporated by reference in its entirely for all purposes. A pilot hole may be drilled prior to insertion of the bone screw 90, or alternatively, the bone screw 90 may be screwed directly into the bone. The pilot hole may be drilled using a standard drill bit straight down opening 84 of the screw hole 80.

At this point in the procedure, the surgeon may reposition bone plate 20, 22 relative to bone screw 90 and the fracture site. Once the position of bone plate 20, 22 has been optimized, bone screws 50 and 100 may be inserted through their respective bone screw holes 52, 102 and driven into the tissue site. The threaded shaft 108 of proximal bone screw 100 engages the threaded side 116 of the wider portion 112 of the screw hole 100. As the bone screw 100 is fully screwed into the bone and the tapered screw head 104 engages the beveled edge 115, the narrower portion 144 provides a compression notch 120, effecting relative longitudinal displacement between the plate 20 and the bone and thereby compressing the fracture or osteotomy. If a locking screw is selected for use in the screw hole 100, fixed angle fixation and compression occur simultaneously. An advantage of this teardrop shaped hole design over the prior art is that compression of the fracture or osteotomy can be obtained while using any style screw, locking or non-locking, providing the surgeon flexibility to select a screw that is most appropriate for the location, health and quality of bone. For example, the option to use a locking screw in soft or osteopenic bone to obtain compression is particularly advantageous.

Figure 10:
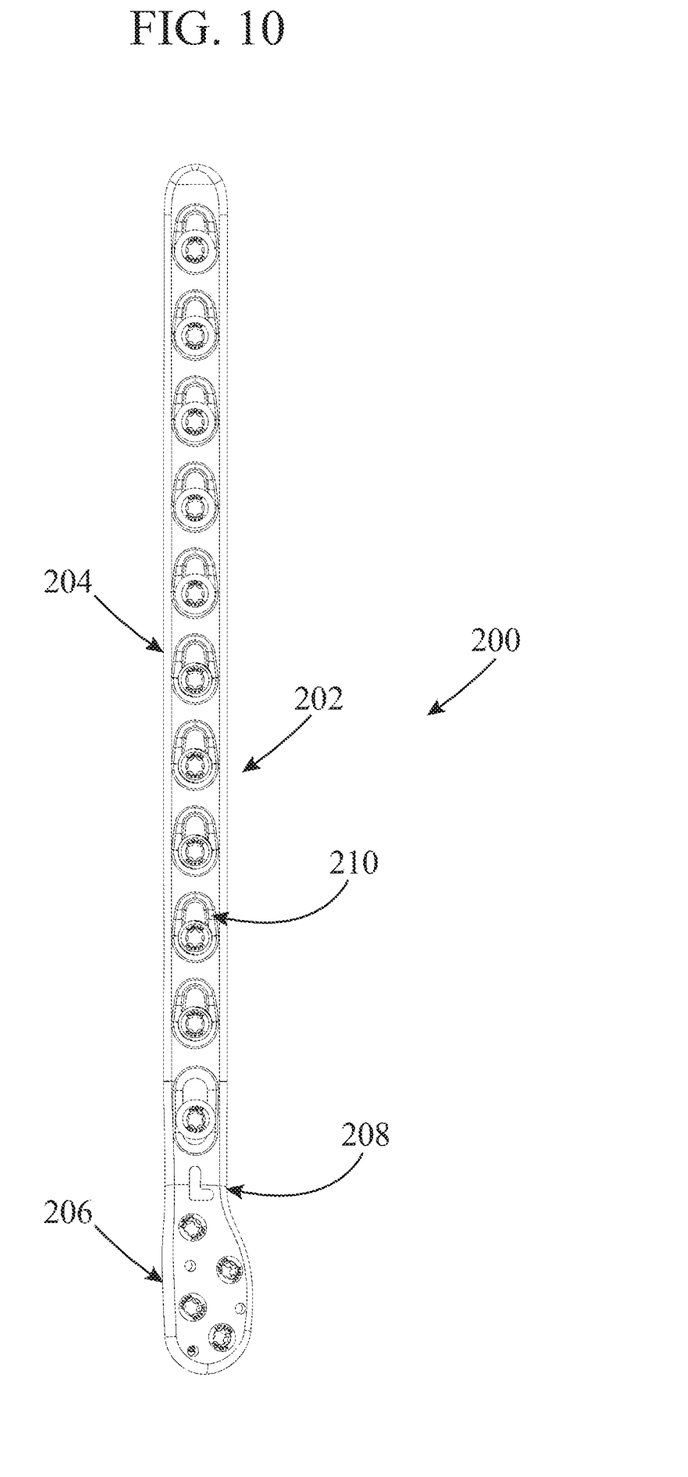
FIG. 10 is a top-down view of a bone plate according to a different embodiment of the present invention.

FIG. 10 illustrates an alternative bone plate 200 according to the present invention for use on the left side of a patient. As shown, bone plate 200 comprises a bone plate body 202 having an elongate proximal portion 204 and distal head portion 206. As in the previous embodiment, bone plate 200 preferably includes an access hole 208 having an inner surface shaped as an L to indicate the correct anatomical location on the patient. Bone plate 200 further includes a plurality of screw holes 210 extending along the proximal portion 204. At least one of the screw holes 210 comprises an adjustable screw hole, as described above in reference to adjustable screw hole 80. Of course, more than one of the screw holes 210 may be adjustable. In certain embodiments, one or more of the screw holes 210 will comprise a versatile screw hole as described above in reference to versatile screw hole 100 such that locking or non-locking screws may be used during the procedure.

Preferred materials for the bone plate and the bone screw are preferably biocompatible materials such as titanium, titanium alloys, steel, cobalt chromium alloys, plastic or composites. According to the invention, the bone plate and the bone screw can also be made of different materials having different mechanical properties.

The description of the invention is provided to enable any person skilled in the art to practice the various embodiments described herein. While the present invention has been particularly described with reference to the various figures and embodiments, it should be understood that these are for illustration purposes only and should not be taken as limiting the scope of the invention.

There may be many other ways to implement the invention. Various functions and elements described herein may be partitioned differently from those shown without departing from the spirit and scope of the invention. Various modifications to these embodiments will be readily apparent to those skilled in the art, and generic principles defined herein may be applied to other embodiments. Thus, many changes and modifications may be made to the invention, by one having ordinary skill in the art, without departing from the spirit and scope of the invention.

A reference to an element in the singular is not intended to mean "one and only one" unless specifically stated, but rather "one or more." The term "some" refers to one or more. Underlined and/or italicized headings and subheadings are used for convenience only, do not limit the invention, and are not referred to in connection with the interpretation of the description of the invention. All structural and functional equivalents to the elements of the various embodiments of the invention described throughout this disclosure that are known or later come to be known to those of ordinary skill in the art are expressly incorporated herein by reference and intended to be encompassed by the invention. Moreover, nothing disclosed herein is intended to be dedicated to the public regardless of whether such disclosure is explicitly recited in the above description.

Other embodiments will be apparent to those skilled in the art from consideration of the specification and practice of the embodiment disclosed herein. It is intended that the specification and examples be considered as exemplary only, with a true scope and spirit of the embodiment being indicated by the following claims.

What is claimed is:

1. A bone plate assembly for the compression of a bone fracture or osteotomy, comprising:
a plate body having a longitudinal axis, a distal end defined by a widest portion of the plate body and extending to a narrower proximal end, an upper surface, a lower bone contacting surface, a plurality of first screw holes arranged in rows at the distal end of the plate body, a second screw hole at the proximal end of the plate body, an access hole between the first and second screw holes, and an adjustable third screw hole extending through the plate body between the access hole and second screw hole, the plate body further comprising a recessed portion in the upper surface surrounding an opening through the plate body defining the adjustable third screw hole,
wherein the access hole is an orientation indicator extending between the upper surface and the lower, bone contacting surface, the access hole having a shape to indicate an anatomical orientation of the bone plate assembly, which anatomical orientation is either a right side or a left side of the patient,
wherein the second screw hole has a main chamber and a narrow portion, the narrow portion being connected to the main chamber in a smooth transition to form a continuous curved opening in the shape of a teardrop, the main chamber defined by a wall having threads while the narrow portion is non-threaded and includes a compression notch; and
wherein the bone plate assembly further comprises a bone screw comprising a head extending into an elongated threaded shank, the head having an outer surface and the elongated threaded shank having a diameter, the bone screw being configured for insertion into the opening of the adjustable third screw hole,
wherein the opening of the adjustable third screw hole is smaller than the outer surface of the head and larger than the diameter of the elongated shank, and
wherein the recessed portion in the upper surface has an inner surface defining an opening in the upper surface of the bone plate, wherein the inner surface of the recessed portion is sized to define a gap around the opening of the adjustable third screw hole and substantially around the entire outer surface of the head of the bone screw to allow for movement of the bone screw within the recessed portion along the longitudinal axis and in at least one direction transverse to the longitudinal axis of the plate body.

2. The bone plate assembly of claim 1, wherein the inner surface of the recessed portion has a substantially oval shape.

3. The bone plate assembly of claim 1, wherein the bone screw is movable in a plurality of directions transverse to the longitudinal axis.

4. The bone plate assembly of claim 1, wherein the outer surface of the bone screw head is substantially conical, the bone screw head further comprising a substantially flat surface opposite the elongated shank and an opening configured for engaging a tool in the substantially flat surface.

5. The bone plate assembly of claim 1, wherein the body plate body is shaped and configured for compression of a distal radius fracture.

6. The bone plate assembly of claim 1, wherein the recessed portion and the adjustable screw hole reside in an elongate proximal portion of the plate body.

7. The bone plate assembly of claim 1, wherein the access hole has the shape of an alphabetical letter.

8. The bone plate assembly of claim 7, wherein the alphabetical letter is an L or R.

9. The bone plate assembly of claim 1, wherein the plate body has a single orientation indicator.

\* \* \* \* \*